United States Patent [19]

Hubele et al.

[11] 4,075,349

[45] Feb. 21, 1978

[54] MICROBICIDAL COMPOSITIONS

[75] Inventors: Adolf Hubele, Magden; Walter Kunz, Oberwil, both of Switzerland; Wolfgang Eckhardt, Lorrach, Germany

[73] Assignee: Ciba-Geigy Corporation, Ardsley, N.Y.

[21] Appl. No.: 726,321

[22] Filed: Sept. 24, 1976

[30] Foreign Application Priority Data

Sept. 30, 1975 Switzerland .................... 12649/75

[51] Int. Cl.$^2$ ................... A01N 9/12; C07C 153/09
[52] U.S. Cl. ................... 424/301; 260/455 R; 260/455 A; 424/300
[58] Field of Search ............... 260/455 R, 455 A; 424/301, 300

[56] References Cited

U.S. PATENT DOCUMENTS

| 3,488,377 | 1/1970 | Krenzer | 260/455 A |
| 3,712,805 | 1/1973 | Yates et al. | 71/100 |
| 3,778,460 | 12/1973 | Wollensak et al. | 260/455 A |
| 3,830,829 | 8/1974 | Olin | 260/455 R |
| 3,832,383 | 8/1974 | Olin | 260/455 R |

OTHER PUBLICATIONS

Reid, "Organic Chemistry of Bivalent Sulfur", vol. II, p. 24, 1960.

*Primary Examiner*—Joseph Paul Brust
*Assistant Examiner*—Robert C. Whittenbaugh
*Attorney, Agent, or Firm*—Harry Falber

[57] ABSTRACT

Acylated thiopropionyl anilines of the formula I shown hereinafter are effective microbicides, preferably for combatting phytopathogenic fungi or for preventing fungi attack.

22 Claims, No Drawings

MICROBICIDAL COMPOSITIONS

The present invention provides compounds of the formula I

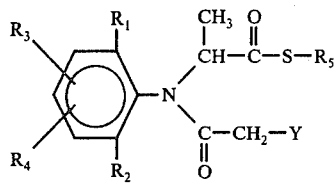

wherein
$R_1$ represents a $C_1$-$C_4$-alkyl group, a $C_1$-$C_4$-alkoxy group or a halogen atom,
$R_2$ represents a $C_1$-$C_3$-alkyl group, a $C_1$-$C_4$-alkoxy group or a halogen atom,
$R_3$ represents a hydrogen atom, a $C_1$-$C_3$-alkyl group or a halogen atom,
$R_4$ represents a hydrogen atom or a methyl group, with the proviso that the total number of carbon atoms contained by the substituents $R_1$, $R_2$, $R_3$ and $R_4$ in the phenyl ring does not exceed 8,
$R_5$ represents a methyl or ethyl group, while
Y represents one of the following groups:
 a. —O—$R_6$
 b. —S—$R_6$, wherein $R_6$ represents alkyl of 1 to 6 carbon atoms, alkenyl of 3 to 6 carbon atoms, or alkinyl of 3 to 6 carbon atoms, or

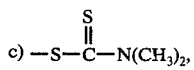

a process for the manufacture thereof, compositions which contain said compounds as active components, and a method of using these active components as microbicides.

By alkyl or alkyl moiety of an alkoxy group are meant the following groups, depending on the stated number of carbon atoms: methyl, ethyl, propyl, iso-propyl, butyl, iso-butyl, sec. butyl, tert. butyl, and pentyl and hexyl and isomers thereof. Alkenyl of 3 to 6 carbon atoms denotes chiefly allyl, methylallyl and pentenyl. Alkinyl of 3 to 6 carbon atoms is chiefly prop-2-inyl (propargyl) and but-2-inyl.

A halogen atom is to be understood as meaning a fluorine, chlorine, bromine or iodine atom.

The present invention is based on the surprising observation that compounds having the structure of formula I possess for practical purposes a very advantageous microbicidal spectrum for protecting cultivated plants. Examples of cultivated plants within the scope of this invention are:
cereals, maize, rice, vegetables, sugar-beet, soya, ground nuts, fruit trees, ornamentals, but primarily vines, hops, cucumber plants (cucumber, marrows, melons), solanaceae, such as potatoes, tobacco plants and tomatoes, and also banana, cocoa and natural rubber plants.

With the active ingredients of the formula I it is possible to inhibit or destroy the fungi which occur in plants or parts of plants (fruit, blossoms, leaves, stems, tubers, roots) in these and also related crops of useful plants, and also to protect from such fungi the parts of plants which grow later. The active ingredients are effective against the phytopathogenic fungi which belong to the following classes: Ascomycetes (e.g. Erysiphaceae); Basidiomycetes, chiefly rust fungi; fungi imperfecti (e.g. Moniliales, and also the genera Cercospora and Fusarium); but especially against the Oomycetes belonging to the class of the Phycomycetes, such as Phytophthora, Peronospora, Pseudoperonospora, Pythium or Plasmopara. In addition, the compounds of the formula I possess a systemic action. They can also be used as seed dressing agents for protecting seeds (fruit, tubers, grains) and plant cuttings from fungus infections and from phytopathogenic fungi which occur in the soil.

Preferred microbicides are compounds of the formula I, wherein $R_1$ represents a methyl or methoxy group and $R_2$ represents a methyl or ethyl group, a chlorine or bromine atom, $R_3$ represents a hydrogen atom, a methyl group, a chlorine or bromine atom, $R_3$ represents a hydrogen atom, a methyl group, a chlorine or bromine atom, and $R_4$ represents a hydrogen atom or a methyl group, and wherein Y represents one of the following groups:
 a'. —$OR_6$ or
 b'. —$SR_6$, wherein $R_6$ represents alkyl of 1 to 6 carbon atoms, allyl or propargyl,

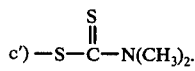

These compounds shall be referred to as group Ia.

An important subgroup of microbicidal compounds in this group Ia comprises those compounds wherein $R_1$ represents a methyl group, $R_2$ represents a methyl or ethyl group or a chlorine atom, each of $R_3$ and $R_4$ independently represents a hydrogen atom or a methyl group, and wherein Y represents —$OR_6$ or —S—$R_6$, wherein $R_6$ represents a methyl, ethyl, propyl, iso-propyl, butyl, sec. butyl or tert. butyl group. These compounds shall be referred to as group Ib. Preferred compounds in this group are thse wherein $R_6$ is a methyl, ethyl, propyl or iso-propyl group.

Another very important subgroup of microbicidal compounds within the group of compounds of the formula I comprises those wherein each of $R_1$ and $R_2$ independently represents a methyl or methoxy group or a halogen atom, $R_3$ represents a hydrogen atom, a methyl group or a halogen atom, $R_4$ represents a hydrogen atom or a methyl group, $R_5$ represents a methyl group and Y represents a $C_1$-$C_3$-alkoxy group, a $C_1$-$C_2$-alkylthio group or a propargyloxy group. These compounds shall be referred to as group Ic.

The compounds of the formula I are obtained according to the invention optionally
 A. by acylating a compound of the formula II

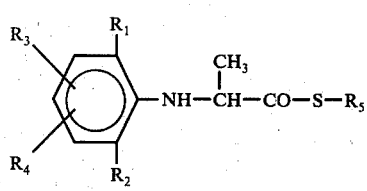

with a compound of the formula III

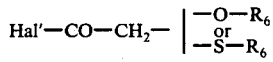 (III)

or

B. by initially monohaloacetylating a compound of the formula II to give a compound of the formula IV

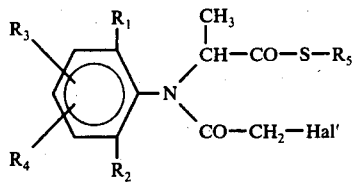 (IV)

and optionally further reacting it with a salt of the N,N-dimethyl-dithiocarbamic acid of the formula V

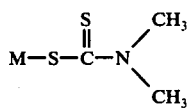 (V)

or with a mercaptan (or the alkali metal salt or alkaline earth metal salt thereof) of the formula

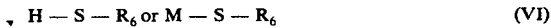 (VI)

In the formulae II, III, IV, V and VI, the symbols $R_1$ to $R_6$ are as defined in formula I, whilst Hal' represents a halogen atom, preferably a chlorine or bromine atom, and M is a metal cation, preferably an alkali metal cation or an alkaline earth metal cation.

The reactions can be carried out in the presence or absence of solvents or diluents which are inert to the reactants. Examples of suitable solvents or diluents are: aliphatic or aromatic hydrocarbons, such as benzene, toluene, xylenes, petroleum ether; halogenated hydrocarbons, such as chlorobenzene, methylene chloride, ethylene chloride, chloroform; ethers and ethereal compounds, such as dialkyl ethers, dioxane, tetrahydrofurane; nitriles, such as acetonitrile; N,N-dialkylated amides, such as dimethyl formamide; dimethyl sulphoxide; ketones, such as methyl ethyl ketone, and mixtures of such solvents.

The reaction temperatures are between 0° and 180° C, preferably between 20° C and 120° C. It is often advantageous to use acid acceptors or condensation agents. Suitable examples are: tertiary amines, for example trialkylamines (e.g. triethylamine), pyridine and pyridine bases, or inorganic bases, for example the oxides and hydroxides, hydrogen carbonates and carbonates of alkali metals and alkaline earth metals, and sodium acetate. Moreover, in the first process (A), it is possible to use an excess of the respective aniline derivative of the formula II as acid acceptor.

Process (A), in which compounds of the formula II are used as starting materials, can also be carried out without acid acceptors. On some occasions it is expedient to introduce nitrogen in order to expel the hydrogen halide that has formed, and on others it is very advantageous to use dimethyl formamide as reaction catalyst.

Particulars on the manufacture of the intermediates of the formula II can be inferred from those methods which are generally indicated for the manufacture of anilinoalkanoic acid esters in the following publications: J.Org. Chem. 30, 4101 (1965); Tetrahedron 1967, 487; Tetrahedron 1967, 493.

The compounds of the formula I contain an asymmetrical carbon atom in the thiopropionate side-chain and can be resolved into the optical antipodes in the customary manner. In this connection, the enantiomeric D-form has the more pronounced microbicidal action.

Within the scope of the invention, those compounds, the compositions which contain them and their use, which refer to the D-configurations of the formula I, are accordingly preferred. These D-forms usually have in ethanol or acetone a negative angle of rotation.

The pure optical D-antipodes are obtained by manufacturing for example the racemic compound of the formula VII

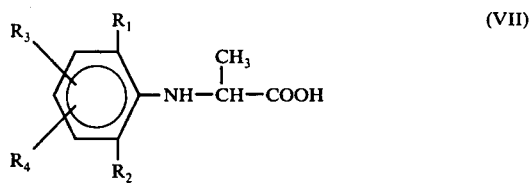 (VII)

wherein $R_1$, $R_2$, $R_3$ and $R_4$ are as defined in formula I, and then reacting it in known manner with a nitrogen-containing optically active base to give the corresponding salt. The pure D-form is obtained stepwise by fractional crystallisation of the salt and subsequent liberation of the acid of the formula VII which is enriched with the optical D-antipode and, if appropriate, repetition (also several times) of the salt formation, crystallisation and liberation of the α-anilino-propionic acid of the formula VII. From this pure D-form it is then possible, if desired, to obtain the optically active ester of the formula II in known manner, for example in the presence of HCl or $H_2SO_4$, with methyl mercaptan or ethyl mercaptan, preferably with their salts, in particular their sodium or potassium salts, and with the acid halide of the optical antipode of the formula VII. This ester is then converted into the optically active end products of the formula I in accordance with the direct method of manufacture (A) or in accordance with method (B), which proceeds by way of haloacetylated intermediate. A suitable optically active organic base is for example α-phenylethylamine.

Instead of the fractional crystallisation, it is also possible to obtain the enantiomeric D-form of the formula II by diazotising the amino group in the naturally occurring L-alanine in the presence, for example, of HCl or HBr, and thereby replacing it by halogen accompanied by the splitting off of $N_2$ and with retention of the L-configuration, then, if appropriate, effecting esterification with methyl mercaptan or ethyl mercaptan, and subsequently reacting the ester with the aniline of the formula VIII

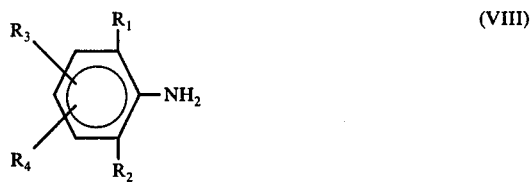 (VIII)

when predominantly inversion to the D-configuration of the formula II occurs (J.Am. Chem. Soc. 76, 6065).

In this manner it is possible to obtain systematically the various diastereoisomers of the formula I.

Irrespective of the cited optical isomerism, an atropisomerism is observed about the phenyl -N< axis in those instances in which the phenyl ring is substituted unsymmetrically to this axis (i.e. optionally also on account of the presence of additional substituents).

Also irrespective of the optical isomerism, where $R_6$ is alkenyl a cis/trans-isomerism can occur at the double bond.

Provided no synthesis with the object of isolating pure isomers is carried out, a product will normally occur as a mixture of two optical isomers, two atropisomers, two cis/trans-isomers or as a mixture of these possible isomers. However, the basically more advantageous fungicidal action of the enantiomeric D-form (in comparison with the D,L-form or with the L-form) is retained and is not noticeably affected by the atropisomerism or the cis/trans-isomerism.

The following Examples will serve to illustrate the invention in more detail but do not limit it to what is described therein. Unless stated to the contrary, an active substance of the formula I is always to be understood as meaning the racemic mixture.

EXAMPLE 1

Manufacture of

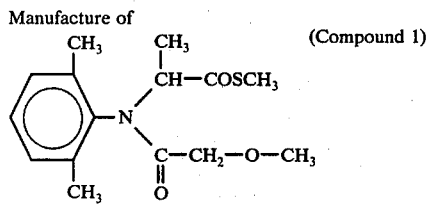

(Compound 1)

N-(1'-Methylthiocarbonyl-ethyl)-N-methoxyacetyl-2,6-dimethylaniline.

a. 24.2 g of 2,6-dimethylaniline, 95.3 g of thiomethyl 2-bromopropionate and 40.2 g of sodium carbonate were stirred for 10 hours at 120° C, and the mixture was then cooled. The reaction mixture was then diluted with 100 ml of water and extracted with diethyl ether. The extract was washed with a small amount of water, dried over sodium sulphate, filtered, and the ether evaporated. Excess thiomethyl 2-bromopropionate was distilled off and the crude product subsequently distilled in a high vacuum; boiling point 125°–127° C/0.1 Torr.

b. 10.9 g of methoxyacetic chloride were slowly added dropwise to 19.2 g of the thiomethyl ester obtained in (a). After the weakly exothermic reaction had subsided, stirring was continued for 8 hours. The reaction mixture was thereafter refluxed for 3 hours, cooled, washed with a small amount of a saturated solution of sodium carbonate and twice with a small amount of water, dried over sodium sulphate and filtered. The solvent was evaporated and the residual oil then crystallised by trituration with a small amount of petroleum ether. After recrystallisation from petroleum ether, the crystals of compound 1 melt at 83°–84° C. The D-forms of the two atropisomers (compounds 3a and 3b) are obtained by acylating the pure D-form of thiomethyl α-(2-methyl-6-ethylanilino)-propionate with methoxyacetic acid or one of the reactive derivatives thereof.

EXAMPLE 2

Manufacture of

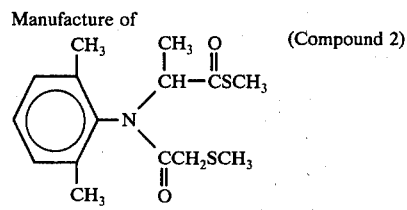

(Compound 2)

N-(1'-Methylthiocarbonyl-ethyl)-N-methylthioacetyl-2,6-dimethylaniline.

While passing in nitrogen and stirring, 3.1 g of methyl mercaptan are introduced into a suspension of 2.8 g of 55% sodium hydride in 150 ml of tetrahydrofurane and subsequently 18 g of N-(1'-methylthiocarbonylethyl)-N-chloroacetyl-2,6-dimethylaniline (prepared by chloroacetylating the intermediate obtained in Example 1a) with, for example, chloroacetyl chloride) in 50 ml of tetrahydrofurane were added dropwise. Stirring was continued for 48 hours at room temperature and the reaction mixture was diluted with 300 ml of diethyl ether, washed three times with water, dried over sodium sulphate and filtered. After recrystallisation from diethyl ether/petroleum ether, compound 2 had a melting point of 88°–92° C.

The following compounds of the formula

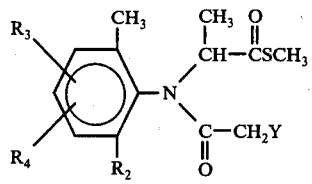

wherein $R_2$ is in 6-position are obtained in this manner by one of the methods indicated above:

| Compound | $R_2$ | $R_3$ | $R_4$ | Y | Physical constant (temperatures in ° C) |
|---|---|---|---|---|---|
| 1 | $CH_3$ | H | H | $-OCH_3$ | m.p. 83–84° |
| 2 | $CH_3$ | H | H | $-SCH_3$ | m.p. 88–92° |
| 3 | $C_2H_5$ | H | H | $-OCH_3$ | b.p. 152°/0.02 Torr. |
| 4 | $C_2H_5$ | H | H | $-SCH_3$ | b.p. 165°/0.2 Torr. |
| 5 | Cl | H | H | $-OCH_3$ | m.p. 70–73° |
| 6 | Cl | H | H | $-SCH_3$ | viscous |
| 7 | $CH_3$ | 3-$CH_3$ | H | $-OCH_3$ | b.p. 140–147°/0.2 Torr. |
| 8 | $CH_3$ | H | H | $-SC_3H_7(n)$ | b.p. 148°/0.04 Torr. |
| 9 | $CH_3$ | H | H | $-OC_2H_5$ | b.p. 153°/0.02 Torr. |
| 10 | $CH_3$ | 3-$CH_3$ | H | $-SCH_3$ | b.p. 153°/0.4 Torr. |
| 11 | $CH_3$ | 3-Br | H | $-OCH_3$ | b.p. 165°/0.1 Torr. |
| 12 | $CH_3$ | 4-Br | H | $-OCH_3$ | b.p. 160°/0.01 Torr. |
| 13 | $C_2H_5$ | H | H | $-SC_3H_7(n)$ | b.p. 163°/0.02 Torr. |
| 14 | $C_2H_5$ | H | H | $-OC_2H_5$ | b.p. 157°/0.02 Torr. |
| 15 | Cl | H | H | $-OC_2H_5$ | b.p. 150–155°/0.03 Torr. |
| 16 | Cl | H | H | $-SC_3H_7(n)$ | viscous |
| 17 | $CH_3$ | 4-Cl | H | $-OCH_3$ | m.p. 104–108° |
| 18 | $CH_3$ | 3-$CH_3$ | H | $-SC_3H_7(n)$ | b.p. 160°/0.02 Torr. |

-continued

| Compound | R₂ | R₃ | R₄ | Y | Physical constant (temperatures in °C) |
|---|---|---|---|---|---|
| 19 | $C_2H_5$ | 4-Br | H | $-OCH_3$ | b.p. 181°/0.4 Torr. |
| 20 | $CH_3$ | 3-Br | H | $-SCH_3$ | b.p. 164°/0.01 Torr. |
| 21 | $CH_3$ | 3-$CH_3$ | H | $-OC_2H_5$ | b.p. 156–161°/0.4 Torr. |
| 22 | $CH_3$ | 4-$CH_3$ | H | $-OCH_3$ | b.p. 167°/0.5 Torr. |
| 23 | $CH_3$ | 4-Br | H | $-SCH_3$ | viscous |
| 24 | $CH_3$ | 3-$CH_3$ | 5-$CH_3$ | $-OCH_3$ | b.p. 174°/0.08 Torr. |
| 25 | $CH_3$ | 3-Br | H | $-OC_2H_5$ | b.p. 161–163°/0.02 Torr. |
| 26 | $CH_3$ | 4-Cl | H | $-SCH_3$ | b.p. 154–159°/0.04 Torr. |
| 27 | $CH_3$ | 3-$CH_3$ | 5-$CH_3$ | $-SC_3H_7(n)$ | oil |
| 28 | $C_2H_5$ | 4-Br | H | $-SCH_3$ | b.p. 185–190°/0.07 Torr. |
| 29 | $CH_3$ | 4-$CH_3$ | H | $-SCH_3$ | m.p. 73–74° |
| 30 | $CH_3$ | 4-Br | H | $-OC_2H_5$ | b.p. 143–146°/0.04 Torr. |
| 31 | $CH_3$ | 4-Cl | H | $-OC_2H_5$ | b.p. 162–165°/0.08 Torr. |
| 32 | $CH_3$ | H | H | $-OC_4H_9(sec)$ | b.p. 173–175°/0.4 Torr. |
| 33 | $CH_3$ | 3-$CH_3$ | 5-$CH_3$ | $-SCH_3$ | viscous |
| 34 | $C_2H_5$ | H | H | $-OC_4H_9(sec)$ | |
| 35 | $C_2H_5$ | 4-Br | H | $-OC_2H_5$ | b.p. 173°/0.07 Torr. |
| 36 | $CH_3$ | H | H | $-OCH_2-CH=CH_2$ | m.p. 82–83° |
| 37 | $CH_3$ | 4-$CH_3$ | H | $-OC_2H_5$ | |
| 38 | Cl | H | H | $-OC_4H_9(sec.)$ | |
| 39 | $CH_3$ | 3-$CH_3$ | 5-$CH_3$ | $-OC_2H_5$ | m.p. 81–83° |
| 40 | $CH_3$ | 4-$CH_3$ | H | $-OC_4H_9(sec.)$ | |
| 41 | $CH_3$ | H | H | $-SC_4H_9(n)$ | |
| 42 | $C_2H_5$ | H | H | $-OCH_2CH=CH_2$ | b.p. 176°/0.07 Torr. |
| 43 | $C_2H_5$ | H | H | $-SC_4H_9(n)$ | |
| 44 | Cl | H | H | $-OCH_2CH=CH_2$ | b.p. 168–171°/0.08 Torr. |
| 45 | $CH_3$ | 4-Br | H | $-SC_4H_9(n)$ | |
| 46 | $CH_3$ | 4-Br | H | $-OCH_2CH=CH_2$ | b.p. 143–146°/0.04 Torr. |
| 47 | $CH_3$ | H | H | $-OC_3H_7(i)$ | b.p. 155°/0.05 Torr. |
| 48 | $CH_3$ | 4-$CH_3$ | H | $-OCH_2-CH=CH_2$ | |
| 49 | Br | 4-Cl | H | $-OCH_3$ | b.p. 164°/0.1 Torr. |
| 50 | $C_2H_5$ | 3-$CH_3$ | H | $-OCH_3$ | b.p. 174°/0.08 Torr. |
| 51 | $C_2H_5$ | H | H | $-OC_3H_7(i)$ | oil |
| 52 | $CH_3$ | H | H | $-SC_2H_5$ | b.p. 148°/0.04 Torr. |
| 53 | Cl | H | H | $-OC_3H_7(i)$ | b.p. 150–155°/0.03 Torr. |
| 54 | $C_2H_5$ | H | H | $-SC_2H_5$ | b.p. 153°/0.3 Torr. |
| 55 | $CH_3$ | 3-$CH_3$ | H | $-OC_3H_7(i)$ | b.p. 160°/0.08 Torr. |
| 56 | Cl | H | H | $-SC_2H_5$ | oil |
| 57 | $CH_3$ | 3-Br | H | $-OC_3H_7(i)$ | b.p. 182–186°/0.02 Torr. |
| 58 | $CH_3$ | 3-$CH_3$ | H | $-SC_2H_5$ | |
| 59 | $CH_3$ | 4-Br | H | $-OC_3H_7(i)$ | viscous |
| 60 | $CH_3$ | 4-Cl | H | $-OC_3H_7(i)$ | oil |
| 61 | $C_2H_5$ | 4-Br | H | $-OC_3H_7(i)$ | |
| 62 | $CH_3$ | 3-Br | H | $-SC_2H_5$ | |
| 63 | $CH_3$ | 4-Br | H | $-SC_2H_5$ | b.p. 176°/0.08 Torr. |
| 64 | $CH_3$ | 4-$CH_3$ | H | $-OC_3H_7(i)$ | |
| 65 | $CH_3$ | 4-Cl | H | $-SC_2H_5$ | |
| 66 | $CH_3$ | 3-$CH_3$ | 5-$CH_3$ | $-OC_3H_7(i)$ | b.p. 168°/0.02 Torr. |
| 67 | $C_2H_5$ | 4-Br | H | $-SC_2H_5$ | |
| 68 | $CH_3$ | H | H | $-OC_3H_7(n)$ | b.p. 156°/0.05 Torr. |
| 69 | $C_2H_5$ | H | H | $-OC_3H_7(n)$ | |
| 70 | $CH_3$ | 4-$CH_3$ | H | $-SC_2H_5$ | |
| 71 | $CH_3$ | 3-$CH_3$ | H | $-OC_3H_7(n)$ | b.p. 166°/0.1 Torr. |
| 72 | $CH_3$ | 3-$CH_3$ | 5-$CH_3$ | $-SC_2H_5$ | |
| 73 | $CH_3$ | 4-Br | H | $-OC_3H_7(n)$ | |
| 74 | Cl | H | H | $-OC_3H_7(n)$ | b.p. 164°/0.08 Torr. |
| 75 | $CH_3$ | H | H | $-OCH_2C\equiv CH$ | m.p. 86–88° |
| 76 | $CH_3$ | 4-$CH_3$ | H | $-OC_3H_7(n)$ | |
| 77 | Cl | H | H | $-SC_3H_7(i)$ | b.p. 151–153°/0.04 Torr. |
| 78 | $C_2H_5$ | H | H | $-OCH_2-C\equiv CH$ | viscous |
| 79 | Br | 4-Br | 3-$CH_3$ | $-OCH_3$ | b.p. 185–192°/0.02 Torr. |
| 80 | $CH_3$ | 4-$CH_3$ | H | $-OCH_2-C\equiv CH$ | m.p. 92–95° |
| 81 | $CH_3$ | H | H | $-SC_3H_7(i)$ | |
| 82 | $CH_3$ | H | H | $-S-\underset{\underset{S}{\|}}{C}-N(CH_3)_2$ | m.p. 138–141° |
| 83 | $CH_3$ | H | H | $-OC_5H_{11}(sec.)$ | |
| 84 | $CH_3$ | 4-$CH_3$ | H | $-SC_3H_7(i)$ | $n_D^{20}$ 1.5533 |
| 85 | $C_2H_5$ | H | H | $-SCN(CH_3)_2$ ‖ S | m.p. 125–128° |

The following compounds of the formula

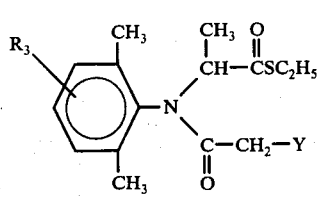

wherein R₂ is in 6-position are obtained in this manner of by one of the methods indicated above:

| Compound | R₃ | Y | Physical constant (temperatures in °C) |
|---|---|---|---|
| 86 | H | $-OCH_3$ | b.p. 154–156°/0.01 Torr. |
| 87 | H | $-OC_2H_5$ | b.p. 158–160°/0.09 Torr. |
| 88 | H | $-SCH_3$ | oil |
| 89 | 3-$CH_3$ | $-OCH_3$ | b.p. 142–148°/0.08 Torr. |
| 90 | 4-Br | $-OCH_3$ | |
| 91 | 3-$CH_3$ | $-OC_2H_5$ | b.p. 158–161°/0.4 Torr. |
| 92 | H | $-SC_2H_5$ | |
| 93 | 4-Br | $-S-C_2H_5$ | |
| 94 | 4-$CH_3$ | $-SC_2H_5$ | oil |

The following compounds of the formula

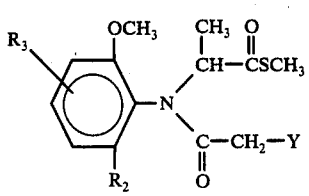

wherein $R_1$ is in 2-position are also obtained in this manner or by one of the methods indicated above:

| Compound | $R_2$ | $R_3$ | Y | Physical constant (temperatures in °C) |
|---|---|---|---|---|
| 95 | $CH_3$ | H | $-OCH_3$ | b.p. 162–168°/0.02 Torr |
| 96 | Br | 4-Br | $-OC_2H_5$ | viscous |
| 97 | $C_2H_5$ | H | $-SCH_3$ | b.p. 168–172°/0.04 Torr |
| 98 | $CH_3$ | 4-Br | $-OCH_3$ | |
| 99 | Br | 4-Cl | $-OC_2H_5$ | oil |
| 100 | $CH_3$ | 4-$CH_3$ | $-OCH_3$ | |
| 101 | $CH_3$ | H | $-OC_3H_7(i)$ | |
| 102 | Cl | H | $-OCH_3$ | m.p. 68–70° |
| 103 | Cl | H | $-SCN(CH_3)_2$ ‖ S | |

It will be readily understood that the compounds of the formula I can be used together with other suitable pesticides, for example fungicides, insecticides, acaricides or active substances which influence plant growth, in order to adapt them to prevailing circumstances and to broaden their activity spectrum.

The compounds of formula I can be used by themselves or together with suitable carriers and/or other additives. Suitable carriers and additives can be solid or liquid and correspond to the customary substances used in the art of formulation, for example natural or regenerated mineral substances, solvents, dispersants, wetting agents, tackifiers, thickeners, binders or fertilisers. The preparation of these compositions is effected in known manner by intimately mixing and grinding the constituents.

For application the active substances may take, and be used in, the following forms:
Solid forms:
  dusts, tracking agents, granules, coated granules, impregnated granules and homogeneous granules.
Liquid forms:
  a. active substance concentrates which are dispersible in water: wettable powders, pastes, emulsions; concentrated solutions.
  b. Solutions: aerosols.

The content of active substance in the above described compositions is between 0.1% and 95%.

For application the active substances of the formula I can be formulated, for example, as follows:
Dusts: The following substances are used to manufacture
a.
  5% and (b) a 2% dust:
a.
  5 parts of active substance
  95 parts of talc;
b.
  2 parts of active substance
  1 part of highly dispersed silicic acid
  97 parts of talc.
The active substances are mixed with the carriers and ground and in this form can be processed to dusts for application.

Granulate: The following substances are used to manufacture a 5% granulate:
  5 parts of active substances
  0.25 parts of epichlorohydrin
  0.25 parts of cetyl polyglycol ether
  3.50 parts of polyethylene glycol
  91 parts of kaolin (particle size 0.3 – 0.8 mm).
The active substance is mixed with epichlorohydrin and the mixture is dissolved in 6 parts of acetone. Then polyethylene glycol and cetyl polyglycol ether are added. The resultant solution is sprayed on kaolin and the acetone is evaporated in vacuo. Such a microgranulate is advantageously used for combating soil fungi.
Wettable powders: The following constituents are used to manufacture (a) a 70%, (b) a 40%, (c) and (d) a 25% and (e) a 10% wettable powder:
a.
  70 parts of active substance
  5 parts of sodium dibutyl naphthylsulphonate
  3 parts of naphthalenesulphonic acid/phenolsulphonic acid/formaldehyde condensate (3:2:1)
  10 parts of kaolin
  12 parts of Champagne chalk
b.
  40 parts of active substance
  5 parts of sodium lignin sulphonate
  1 part of sodium dibutylnaphthalenesulphonic acid
  54 parts of silicic acid
c.
  25 parts of active substance
  4.5 parts of calcium lignin sulphonate
  1.9 parts of Champagne chalk/hydroxyethyl cellulose mixture (1:1)
  1.5 parts of sodium dibutylnaphthalenesulphonate
  19.5 parts of silicic acid
  19.5 parts of Champagne chalk
  28.1 parts of kaolin
d.
  25 parts of active substance
  2.5 parts of isooctylphenoxy-polyethylene-ethanol
  1.7 parts of a Champagne chalk/hydroxyethyl cellulose mixture (1:1)
  8.3 parts of sodium aluminium silicate
  16.5 parts of kieselguhr
  46 parts of kaolin
e.
  10 parts of active substance
  3 parts of a mixture of the sodium salts of saturated fatty alcohol sulphates
  5 parts of naphthalenesulphonic acid/formaldehyde condensate
  82 parts of kaolin.
The active substances are intimately mixed in suitable mixers with the additives and ground in appropriate mills and rollers. Wettable powders of excellent wettability and suspension powder are obtained. These wettable powders can be diluted with water to give suspensions of the desired concentration and can be used in particular for leaf application.
Emulsifiable concentrates: The following substances are used to manufacture a 25% emulsifiable concentrate:
  25 parts of active substance
  2.5 parts of epoxidised vegetable oil
  10 parts of an alkylarylsulphonate/fatty alcohol polyglycol ether mixture
  5 parts of dimethyl formamide
  57.5 parts of xylene.

By diluting such concentrates with water it is possible to manufacture emulsions of the desired concentration, which are especially suitable for leaf application.

The nearest comparable compounds of the prior art cited in U.S. Pat. No. 3,712,805, for example N-(4-chloro-2-methylphenoxyacetyl)-N-(3,4-dichlorophenyl)-alanine ethyl ester in Table 1, possess a herbicidal but not a fungicidal action. The following tests illustrate the pronounced fungicidal action of the compounds of the formula I on plants, whilst no damage to the plants themselves was observed.

EXAMPLE 3

Action on Phytophthora infestans on tomato plants

Ia. Residual preventive action

Tomato plants of the "Roter Gnom" variety are infected when 3 weeks old with a zoospore suspension of Phytophthora infestans after they have been sprayed with a broth (prepared from the active substance formulated as a wettable powder) containing 0.05% of active substance, and dried. The plants are then kept for 6 days in a climatic chamber at 18° to 20° C and high humidity, which is produced by means of an artificial wet fog. After this time typical leaf specks appear. The effectiveness of the tested substance is assessed by determining the number and size of these specks.

Ib. Curative Action

"Roter Gnom" tomato plants are sprayed when 3 weeks old with a zoospore suspension of the fungus and incubated in a climatic chamber at 18° to 20° C and saturated humidity. The humidifying is interrupted after 24 hours. After the plants have dried, they are sprayed with a broth which contains the active substance formulated as a wettable powder in a concentration of 0.05%. After the spray coating has dried, the plants are again kept in the humid chamber for 4 days. The effectiveness of the tested substances is assessed by determining the size and number of the typical leaf specks which have occurred during this time.

II. Preventive-systemic action

The active substance is applied as a wettable powder in a concentration of 0.05% (referred to the volume of the soil) to the surface of the soil of 3 weeks of "Roter Gnom" tomatoes in pots. Three days later the underside of the leaves of the plants are sprayed with a zoospore suspension of Phytophthora infestans. The plants are then kept in a spray chamber at 18° to 20° C and saturated humidity for 5 days, after which time typical leaf specks form. The effectiveness of the tested substance is assessed by determining the size and number of the specks.

In these three tests, the compounds of the formula I effected a pronounced leaf-fungicidal action.

Compounds 1 to 7, 9, 10, 12, 14, 15, 17, 21, 23, 24, 25, 26, 30, 31, 35, 36, 39, 42, 44, 46, 47, 49 to 53, 55, 56, 57, 59, 60, 68, 74, 75, 78, 79, 80, 82, 86, 87, 88, 89, 91, 95, 96, 99 and 102 reduced the fungus attack to less than 20% and to a partial extent inhibited it completely. Infected, untreated tomato plants were used as controls (=100% attack).

EXAMPLE 4

Action on Plasmopara viticola (Bert. et Curt.) (Berl. et de Toni) on vines a. Residual preventive action Vine cuttings of the variety "Chasselas" were reared in a greenhouse. Three plants in the 10 leaf stage were sprayed with a broth (containing 0.05% of active substance) prepared from the active substance and formulated as a wettable powder. After the coating layer had dried, the plants were infected on the underside of the leaves with the spore suspension of the fungus. The plants were subsequently kept in a humid chamber for 8 days, after which time symptoms of the disease were visible on the control plants. The effectiveness of the tested substances were assessed by determining the number and size of the infected areas on the treated plants.

b. Curative action

Vine cuttings of the variety "Chasselas" were reared in a greenhouse and infected in the 10 leaf stage on the underside of the leaves with a spore suspension of Plasmopara viticola. After they had been kept for 24 hours in a humid chamber, the plants were sprayed with a 0.05% broth prepared from a wettable powder of the active substance.

The plants were then kept in a humid chamber for a further 7 days, after which time the symptoms of the desease were visible on the control plants. The effectiveness of the tested substances was assessed by determining the size and number of the infected areas.

In both these tests the compounds of the formula I effected a good leaf-fungicidal action. The fungus attack was reduced on average to less than 20% in comparison with control plants. Compounds of the subgroup Ic were particularly effective. Many of the compounds, for example compounds 1, 2, 3, 7, 21, 36, 47, 55, 75, 86, 89, 95 and 102, controlled the fungus attack completely or almost completely even in concentrations of 0.02% (0-5% attack).

EXAMPLE 5

Action on Pythium debaryanum on sugar beets (Beta vulgaris)

a. Action after soil application

The fungus is cultivated on sterile oat grains and added to a mixture of earth and sand. Lower pots are filled with the infected soil in which sugar beet seeds are then sown. Immediately after sowing, the test preparations formulated as wettable powders are poured in the form of aqueous suspensions over the soil (20 ppm of active substance referred to the volume of the soil). The pots are then stood for 2-3 weeks in a greenhouse at 20°-24° C. The soil is kept uniformly moist by gently spraying it with water. The emergence of the sugar beet plants as well as the number of healthy and sick plants are ascertained in evaluating the tests.

b. Action after seed dressing application

The fungus is cultivated on sterile oat grains and added to a mixture of earth and sand. Flower pots are filled with the infected soil and sugar beet seeds which have been treated with the test preparations formulated as seed dressing powders are sown therein (1000 ppm of active substance referred to the weight of the seeds). The pots are then stood in a greenhouse for 2-3 weeks at 20°-24° C. The soil is kept uniformly moist by gently spraying it with water. The emergence of the sugar beet plants as well as the number of healthy and sick plants are ascertained. Under the conditions of both test (a) and test (b), more than 80% of the sugar beet plants emerged after treatment with the active substances of the formula I and had a healthy appearance.

The pronounced action of compounds 2 and 47, which completely supresses a Pythium infection, is to be singled out for particular mention.

EXAMPLE 6

Action on Cercospora arachidicola on ground nut plants (Arachis hypogaea)

Residual protective action

Ground nut plants, 10 to 15 cm in height, were sprayed with a spray broth (containing 0.02% of active substance) prepared from a wettable powder of the active substance, and 48 hours later infected with a conidia suspension of the fungus. The infected plants were incubated for 24 hours at approx. 21° C and high humidity and subsequently stood in a greenhouse until the occurrence of the typical leaf specks. The evaluation of the fungicidal action, based on the number and size of the specks, was made 12 days after the infection.

In comparison with infected, untreated control plants, the fungus attack was markedly inhibited in plants treated with active compounds of the formula I, in particular when using compounds 2 and 10 (attack 0–5%).

EXAMPLE 7

Action on Erisyphe graminis on barley (Hordeum vulgare)

Residual protective action

Barley plants approx. 8 cm in height were sprayed with a spray broth (0.05% of active substance) prepared from a wettable powder of the active substance. After 48 hours the treated plants were dusted with conidia of the fungus. The infected barley plants were stood in a greenhouse at approx. 22° C and the fungus infection was evaluated after 10 days.

In comparison with infected, untreated control plants, treatment with active compounds of the formula I effected a pronounced inhibition of the fungus attack.

EXAMPLE 8

Action on Fusarium oxysporum in tomato plants

Activity in the soil

The roots of 3 week old tomato plants were damaged and infected with a spore suspension of the wilt-inducing pathogen. After 24 hours, the infected tomato plants were soaked with a spray broth prepared from a wettable powder of the active substance (0.006%, referred to the volume of the soil). The degree of wilting of the plants was evaluated after they had been incubated for 14 days in a greenhouse at approx. 22° C.

In comparison with infected, untreated control plants, treatment with active compounds of the formula I strongly inhibited the fungus attack, in particular when using compounds 1 and 3. The treated plants had a uniformly healthy appearance.

We claim:

1. A compound of the formula I

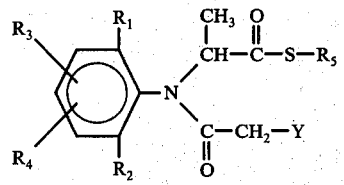

wherein
- $R_1$ represents a $C_1$-$C_4$-alkyl group, a $C_1$-$C_4$-alkoxy group or a halogen atom,
- $R_2$ represents a $C_1$-$C_3$-alkyl group, a $C_1$-$C_4$-alkoxy group or a halogen atom,
- $R_3$ represents a hydrogen atom, a $C_1$-$C_3$-alkyl group or a halogen atom,
- $R_4$ represents a hydrogen atom or a methyl group, with the proviso that the total number of carbon atoms contained by the substituents $R_1$, $R_2$, $R_3$ and $R_4$ in the phenyl ring does not exceed 8,
- $R_5$ represents a methyl or ethyl group, while
- Y represents one of the following groups:
  - a. —O—$R_6$
  - b. —S—$R_6$, wherein $R_6$ represents alkyl of 1 to 6 carbon atoms, alkenyl of 3 to 6 carbon atoms, or alkinyl of 3 to 6 carbon atoms, or c) 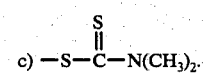

2. The compound of the formula I according to claim 1, wherein $R_1$ represents a methyl or methoxy group and $R_2$ represents a methyl or ethyl group, a chlorine or bromine atom, $R_3$ represents a hydrogen atom, a methyl group, a chlorine or bromine atom, and $R_4$ represents a hydrogen atom or a methyl group, and wherein Y represents one of the following groups:
- a'. —O$R_6$ or
- b'. —S$R_6$, wherein $R_6$ represents alkyl of 1 to 4 carbon atoms, allyl or propargyl, c') 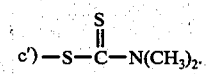

3. The compound according to claim 2, wherein $R_1$ represents a methyl group, $R_2$ represents a methyl or ethyl group of a chlorine atom, each of $R_3$ and $R_4$ independently represents a hydrogen atom or a methyl group, and wherein Y represents —O$R_6$ or —S—$R_6$, in which $R_6$ represents a methyl, ethyl, propyl, iso-propyl, butyl, sec. butyl or tert. butyl group.

4. The compound according to claim 3, wherein $R_6$ represents a methyl, ethyl, propyl or iso-propyl group.

5. The compound of the formula I according to claim 1, wherein each of $R_1$ and $R_2$ independently represents a methyl or methoxy group or a halogen atom, $R_3$ represents a hydrogen atom, a methyl group or a halogen atom, $R_4$ represents a hydrogen atom or a methyl group, $R_5$ represents a methyl group and Y represents a $C_1$-$C_3$-alkoxy group, a $C_1$-$C_2$-alkylthio group or a propargyloxy group.

6. N-(1'-Methylthiocarbonyl-ethyl)-N-methoxyacetyl-2,6-dimethylaniline according to claim 1.

7. N-(1'-Methylthiocarbonyl-ethyl)-N-methylthioacetyl-2,6-dimethylaniline according to claim 1.

8. N-(1'-Methylthiocarbonyl-ethyl)-N-methoxyacetyl-2-methyl-6-ethylaniline according to claim 1.

9. N-(1'-Methylthiocarbonyl-ethyl)-N-methoxyacetyl-2-methyl-6-chloroaniline according to claim 1.

10. N-(1'-Methylthiocarbonyl-ethyl)-N-methoxyacetyl-2,3,6-trimethylaniline according to claim 1.

11. N-(1'-Methylthiocarbonyl-ethyl)-N-methoxyacetyl-2,6-dimethyl-4-chloroaniline according to claim 1.

12. N-(1'-methylthiocarbonyl-ethyl)-N-ethoxyacetyl-2,3,6-trimethylaniline according to claim 1.

13. N-(1'-Methylthiocarbonyl-ethyl)-N-isopropoxyacetyl-2,6-dimethylaniline according to claim 1.

14. N-(1'-methylthiocarbonyl-ethyl)-N-propargyloxyacetyl-2,6-dimethylaniline according to claim 1.

15. N-(1'-ethylthiocarbonyl-ethyl)-N-methoxyacetyl-2,6-dimethylaniline according to claim 1.

16. N-(1'-Methylthiocarbonyl-ethyl)-N-methoxyacetyl-2-chloro-6-methoxyaniline according to claim 1.

17. A composition for controlling fungi and bacteria, which contains as active an effective amount of a compound of the formula I

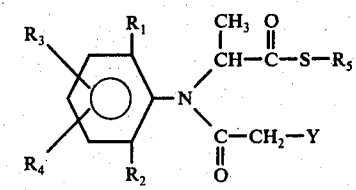

wherein
   $R_1$ represents a $C_1$-$C_4$-alkyl group, a $C_1$-$C_4$-alkoxy group or a halogen atom,
   $R_2$ represents a $C_1$-$C_3$-alkyl group, a $C_1$-$C_4$-alkoxy group or a halogen atom,
   $R_3$ represents a hydrogen atom, a $C_1$-$C_3$-alkyl group or a halogen atom,
   $R_4$ represents a hydrogen atom or a methyl group, with the proviso that the total number of carbon atoms contained by the substitutents $R_1$, $R_2$, $R_3$ and $R_4$ in the phenyl ring does not exceed 8,
   $R_5$ represents a methyl or ethyl group, whilst
   Y represents one of the following groups:
   a. —O—$R_6$
   b. —S—$R_6$, wherein $R_6$ represents alkyl of 1 to 6 carbon atoms, alkenyl of 3 to 6 carbon atoms, or alkinyl of 3 to 6 carbon atoms, or c) 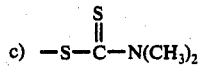

together with suitable carriers.

18. A composition according to claim 17, which contains a compound of the formula I, wherein $R_1$ represents a methyl or methoxy group and $R_2$ represents a methyl or ethyl group, a chlorine or bromine atom, $R_3$ represents a hydrogen atom, a methyl group, a chlorine or bromine atom, and $R_4$ represents a hydrogen atom or a methyl group, and wherein Y represents one of the following groups:
   a'. —O$R_6$ or
   b'. —S$R_6$, wherein $R_6$ represents alkyl of 1 to 4 carbon atoms, allyl or propargyl, c') 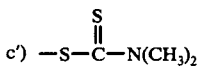

19. A composition according to claim 18, which contains a compound of the formula I, wherein $R_1$ represents a methyl group, $R_2$ represents a methyl or ethyl group or a chlorine atom, each of $R_3$ and $R_4$ independently represents a hydrogen atom or a methyl group, and wherein Y represents —O$R_6$ or —S—$R_6$, in which $R_6$ represents a methyl, ethyl, propyl, isopropyl, butyl, sec. butyl or tert. butyl group.

20. A composition according to claim 19, wherein $R_6$ represents a methyl, ethyl, propyl or iso-propyl group.

21. A composition according to claim 17, which contains a compound of the formula I, wherein each of $R_1$ and $R_2$ independently represents a methyl or methoxy group or a halogen atom, $R_3$ represents a hydrogen atom, a methyl group or a halogen atom, $R_4$ represents a hydrogen atom or a methyl group, $R_5$ represents a methyl group and Y represents a $C_1$-$C_3$-alkoxy group, a $C_1$-$C_2$-alkylthio group or a propargyloxy group.

22. A method of combatting phytopathogenic fungi or of preventing attack by fungi, which comprises applying to plants or parts of plants a fungicidally effective, non-phytotoxic amount of a compound of the formula I according to claim 1.

UNITED STATES PATENT OFFICE
CERTIFICATE OF CORRECTION

Patent No. 4,075,349  Dated February 21, 1978

Inventor(s) Adolf Hubele et al.

It is certified that error appears in the above-identified patent and that said Letters Patent are hereby corrected as shown below:

In the claims, Claim 17, Column 15, Line 26 should appear as follows:

$R_1$ represents a $C_1$-$C_4$-alkyl group, a $C_1$-$C_4$-alkoxy

Signed and Sealed this

Eleventh Day of July 1978

[SEAL]

Attest:

RUTH C. MASON
Attesting Officer

DONALD W. BANNER
Commissioner of Patents and Trademarks